(12) United States Patent
Lester et al.

(10) Patent No.: US 11,806,038 B2
(45) Date of Patent: Nov. 7, 2023

(54) SURGICAL INSTRUMENT AND METHOD FACILITATING TESTING JAW FORCE OF THE SURGICAL INSTRUMENT

(71) Applicant: Covidien LP, Mansfield, MA (US)

(72) Inventors: Matthias Lester, Longmont, CO (US); Jeremy P. Green, Westminster, CO (US); Kenneth E. Netzel, Loveland, CO (US)

(73) Assignee: Covidien LP, Mansfield, MA (US)

( * ) Notice: Subject to any disclaimer, the term of this patent is extended or adjusted under 35 U.S.C. 154(b) by 616 days.

(21) Appl. No.: 17/061,822

(22) Filed: Oct. 2, 2020

(65) Prior Publication Data

US 2021/0106353 A1 Apr. 15, 2021

Related U.S. Application Data

(60) Provisional application No. 62/913,881, filed on Oct. 11, 2019.

(51) Int. Cl.
| | |
|---|---|
| *A61B 17/32* | (2006.01) |
| *A61B 17/28* | (2006.01) |
| *A61B 90/00* | (2016.01) |
| *A61B 17/00* | (2006.01) |

(52) U.S. Cl.
CPC .... *A61B 17/320092* (2013.01); *A61B 17/282* (2013.01); *A61B 90/06* (2016.02); *A61B 2017/00022* (2013.01); *A61B 2090/064* (2016.02); *A61B 2562/0252* (2013.01)

(58) Field of Classification Search
CPC ............ A61B 90/06; A61B 17/320092; A61B 17/282; A61B 2090/064; A61B 2562/0252; A61B 2017/00022
USPC ......................................................... 73/1.01
See application file for complete search history.

(56) References Cited

U.S. PATENT DOCUMENTS

| | | |
|---|---|---|
| 4,022,453 A | 5/1977 | Durgan |
| 4,270,390 A | 6/1981 | Kimball et al. |
| 5,954,460 A | 9/1999 | Degen et al. |
| 6,582,451 B1 | 6/2003 | Marucci et al. |
| 7,731,717 B2 | 6/2010 | Odom et al. |
| 7,776,037 B2 | 8/2010 | Odom |
| 7,982,477 B2 | 7/2011 | Ghadaksaz |
| 8,034,049 B2 | 10/2011 | Odom et al. |
| 8,215,182 B2 | 7/2012 | Artale et al. |
| 8,382,754 B2 | 2/2013 | Odom et al. |
| 8,439,913 B2 | 5/2013 | Horner et al. |
| 9,247,988 B2 | 2/2016 | McKenna et al. |
| 9,603,652 B2 | 3/2017 | Carlton et al. |
| 9,636,167 B2 * | 5/2017 | Gregg .................... A61B 17/00 |
| 9,642,665 B2 | 5/2017 | Weinberg et al. |
| 9,839,467 B2 | 12/2017 | Harper et al. |
| 9,918,783 B2 | 3/2018 | Horner et al. |
| 10,117,705 B2 | 11/2018 | Chernov et al. |
| 10,130,413 B2 | 11/2018 | Brandt et al. |

(Continued)

*Primary Examiner* — Nathaniel T Woodward
(74) *Attorney, Agent, or Firm* — Carter, DeLuca & Farrell LLP

(57) ABSTRACT

A method of testing a jaw force of an ultrasonic surgical instrument includes securing a blade of an end effector of the ultrasonic surgical instrument, clamping a jaw member of the end effector against the blade such that a sensor is received within a notch of the jaw member of the end effector, and measuring the jaw force of the end effector using the sensor.

14 Claims, 6 Drawing Sheets

(56) References Cited

U.S. PATENT DOCUMENTS

| | | |
|---|---|---|
| 10,245,104 B2 | 4/2019 | McKenna et al. |
| 10,335,226 B2 | 7/2019 | Harper et al. |
| 10,368,898 B2 | 8/2019 | Brown et al. |
| 2009/0204114 A1 | 8/2009 | Odom |
| 2010/0217264 A1 | 8/2010 | Odom et al. |
| 2011/0036183 A1* | 2/2011 | Artale .................... A61B 90/06 73/862.621 |
| 2015/0223868 A1 | 8/2015 | Brandt et al. |
| 2016/0045248 A1 | 2/2016 | Unger et al. |
| 2016/0089198 A1 | 3/2016 | Arya et al. |
| 2016/0346034 A1 | 12/2016 | Arya et al. |
| 2017/0079740 A1 | 3/2017 | Hufnagel et al. |
| 2017/0215943 A1 | 8/2017 | Allen, IV |
| 2017/0215944 A1 | 8/2017 | Keffeler |
| 2019/0083168 A1* | 3/2019 | Wham ................ A61B 18/1445 |
| 2019/0282296 A1 | 9/2019 | Harper et al. |

* cited by examiner

SURGICAL INSTRUMENT AND METHOD FACILITATING TESTING JAW FORCE OF THE SURGICAL INSTRUMENT

CROSS-REFERENCE TO RELATED APPLICATIONS

This application claims the benefit of and priority to U.S. Provisional Patent Application Ser. No. 62/913,881 filed Oct. 11, 2019, the entire disclosure of which is incorporated by reference herein.

FIELD

The present disclosure is generally related to the field of surgical instruments, and more particularly to a surgical instruments and methods of facilitating testing a jaw force of the surgical instrument.

BACKGROUND

Surgical instruments utilize ultrasonic energy, e.g., ultrasonic vibrations, to treat tissue, such as, for example ultrasonic surgical instruments. More specifically, ultrasonic surgical instruments utilize mechanical vibration energy transmitted at ultrasonic frequencies to coagulate, cauterize, fuse, seal, cut, desiccate, fulgurate, or otherwise treat tissue. Typically, an ultrasonic surgical instrument is configured to transmit ultrasonic energy produced by a generator and transducer assembly along a waveguide to an end effector which includes a blade and a jaw member configured to clamp and treat tissue between the blade and the jaw member.

SUMMARY

In aspects, the present disclosure provides a method of testing a jaw force of an ultrasonic surgical instrument. The method includes securing a blade of an end effector of the ultrasonic surgical instrument; clamping a jaw member of the end effector against the blade such that a sensor is received within a notch of the jaw member of the end effector; and measuring the jaw force of the end effector using the sensor.

In aspects, the method may further include determining a distance of the sensor from a jaw pivot point of the end effector.

In aspects, securing the blade may include inserting the blade into a fixture configured to hold the blade in place.

In aspects, the sensor is a force sensor.

In aspects, the sensor is a load cell.

In aspects, the measured jaw force may be the manufactured clamping force of the end effector.

In aspects, the method may further include determining if the manufactured clamping force of the end effector is within a predetermined range.

In aspects, the jaw member may include a support base and a jaw liner, the notch may be defined within the support base, and the jaw liner may be configured to clamp against the blade.

In another aspect, the disclosure provides an ultrasonic system including an ultrasonic surgical instrument having an end effector configured to treat tissue between a jaw member and a blade of the end effector; a sensor configured for insertion into a notch of the jaw member for measurement of the jaw force of the end effector between the jaw member and the blade; and a fixture configured to secure the blade of the end effector.

In aspects, the sensor may be further configured to determine a distance from the sensor to a jaw pivot point of the end effector.

In aspects, the sensor may be a force sensor.

In aspects, the sensor may be a load cell.

In aspects, the measured jaw force may be the manufactured clamping force of the end effector.

In aspects, the jaw member may include a support base and a jaw liner, the notch may be defined within the support base, and the jaw liner may be configured to clamp against the blade.

In aspects, the clamping force of the end effector is compared to a predetermined ranged.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Particular embodiments of the disclosure are described hereinbelow with reference to the accompanying drawings. In the following description, well-known functions or constructions are not described in detail to avoid obscuring the disclosure in unnecessary detail. As used herein, the term "distal" refers to that portion which is further from the user while the term "proximal" refers to that portion which is closer to the user or surgeon.

Surgical instruments and methods for facilitating testing of a jaw force of the surgical instrument are provided in accordance with the present disclosure and described in detail below. The particular illustrations and embodiments disclosed herein are merely exemplary and do not limit the scope or applicability of the present disclosure. In particular, the illustration of the surgical instrument shows an instrument with a straight blade, however, other configurations of the surgical instrument are realized. For example, surgical instruments including a curved blade may equally be applicable such as the surgical instrument described in U.S. Pat. No. 10,368,898, which is hereby incorporated by reference herein in its entirety.

Figure 1A:
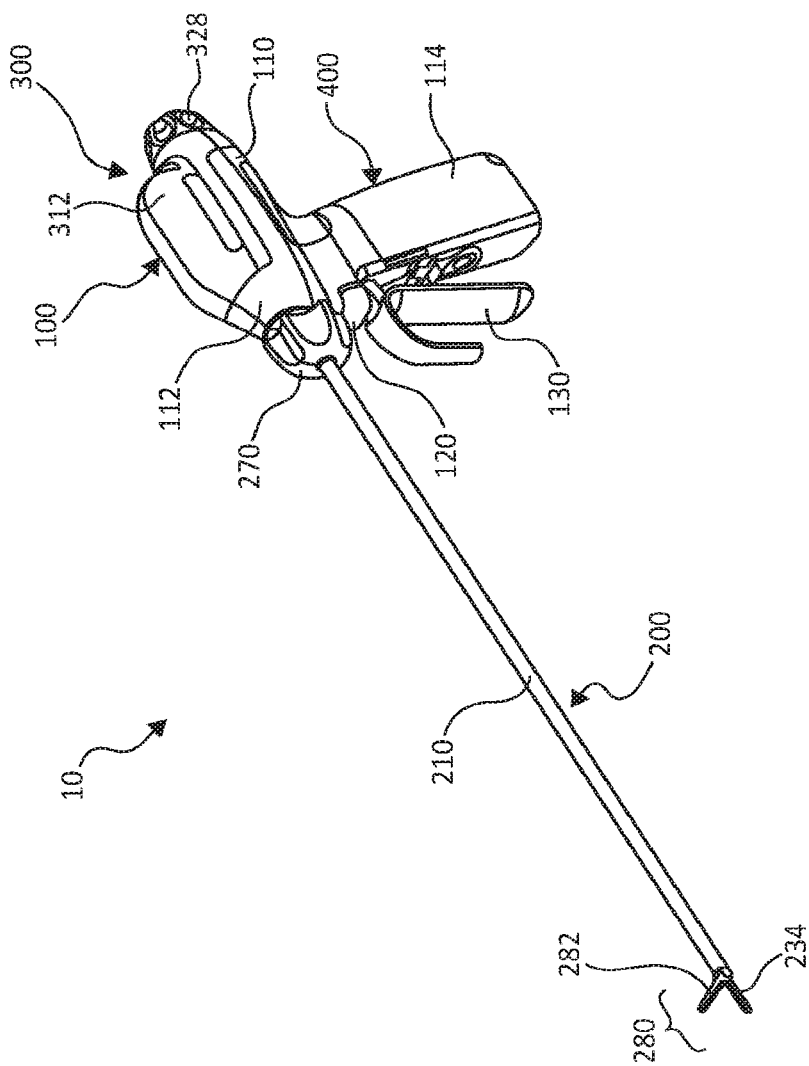
FIG. 1A is a perspective view that illustrates an ultrasonic surgical instrument according to the disclosure, including an elongated assembly, a handle assembly, and an end effector thereof disposed in an open position.
Figure 1B:
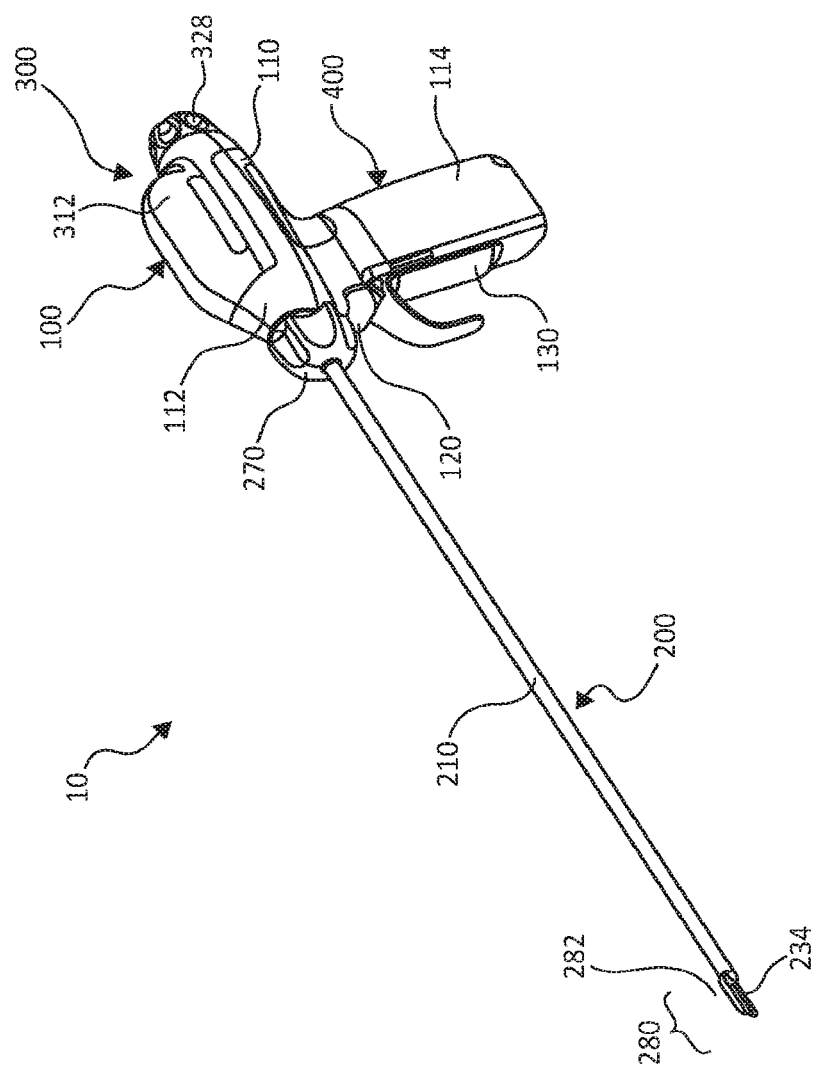
FIG. 1B is a perspective view of the ultrasonic surgical instrument of FIG. 1A, depicted with the end effector disposed in a clamping position.
Figure 2:
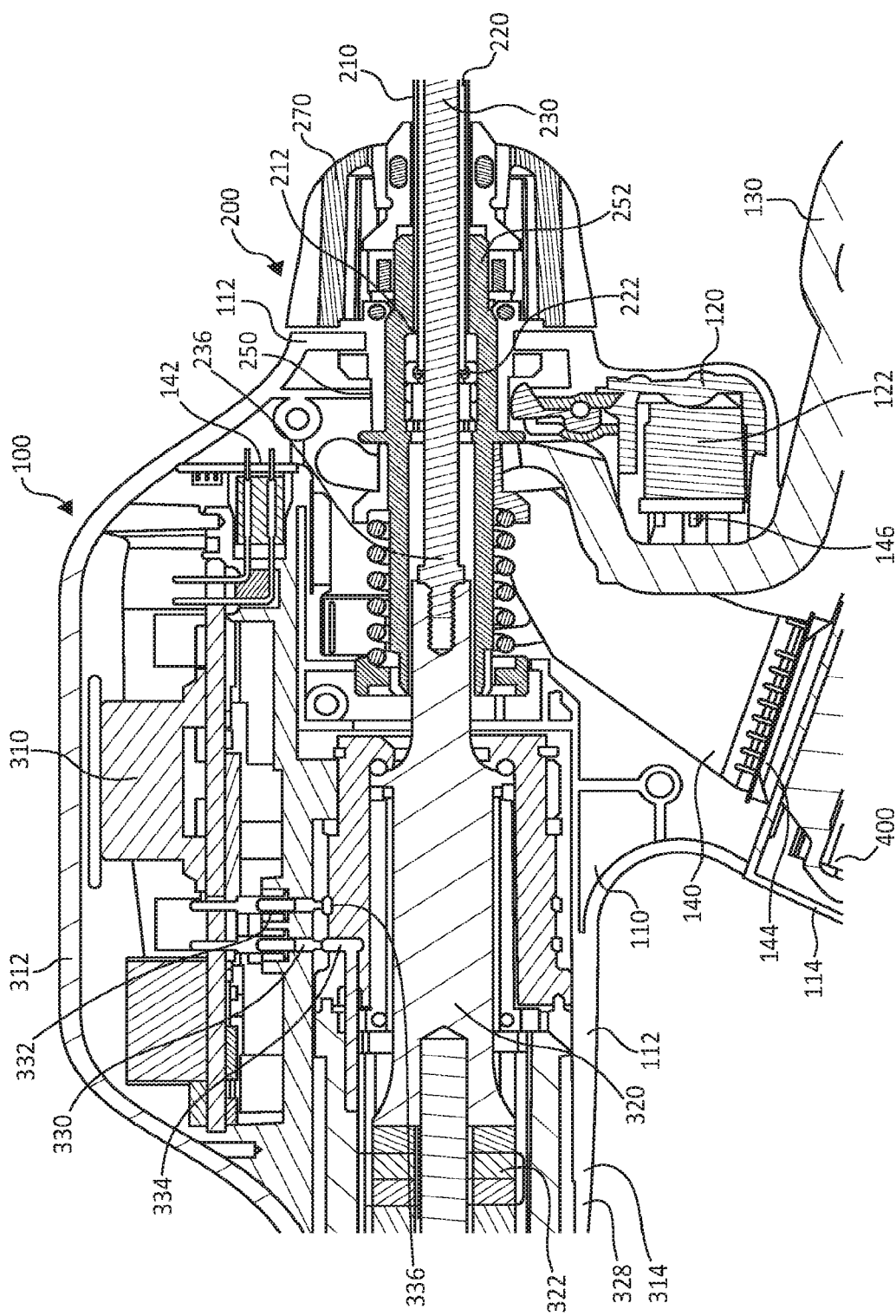
FIG. 2 is an enlarged, side, cross-sectional view of a proximal portion of the ultrasonic surgical instrument of FIG. 1A.

Referring initially to FIGS. 1A, 1B, and 2, a surgical instrument, such as, for example, an ultrasonic surgical instrument 10 generally includes a handle assembly 100 and an elongated assembly 200 that is configured to engage (releasably or permanently) handle assembly 100. The surgical instrument is detailed herein as an ultrasonic surgical instrument, however, other suitable surgical instruments are also contemplated Handle assembly 100 includes a housing 110 defining a body portion 112 configured to support an ultrasonic transducer and generator assembly ("TAG") 300, and a fixed handle portion 114 configured to receive a battery assembly 400. Handle assembly 100 further includes an activation button 120 operably positioned to electrically couple between TAG 300 and battery assembly 400 when TAG 300 is mounted on body portion 112 of housing 110 and battery assembly 400 is engaged within housing 110.

A clamp trigger 130 extends from housing 110 of handle assembly 100 adjacent fixed handle portion 114 of housing 110. An electrical connector 140 disposed within housing 110 of handle assembly 100 includes TAG contacts 142, battery assembly contacts 144, and an activation button connector 146. Electrical connector 140 electrically couples to activation button 120 via activation button connector 146, is configured to electrically couple to TAG 300 via TAG contacts 142 upon engagement of TAG 300 with body portion 112 of housing 110 of handle assembly 100, and is configured to electrically couple to battery assembly 400 via battery assembly contacts 144 upon engagement of battery assembly 400 within housing 110 of handle assembly 100. As such, in use, when activation button 120 is activated in an appropriate manner, an underlying two-mode switch assembly 122 is activated to supply power from battery assembly 400 to TAG 300 in either a "LOW" power mode or a "HIGH" power mode, depending upon the manner of activation of activation button 120.

TAG 300 includes a generator 310 and an ultrasonic transducer 320. Generator 310 includes a housing 312 configured to house the internal electronics of generator 310, and a cradle 314 configured to rotatably support ultrasonic transducer 320. A set of connectors 330, 332 and corresponding rotational contacts 334, 336 associated with generator 310 and ultrasonic transducer 320, respectively, enable drive signals to be communicated from generator 310 to a piezoelectric sack 322 to drive ultrasonic transducer 320. Ultrasonic transducer 320 further includes a rotation knob 328 disposed at a proximal end thereof to enable rotation of ultrasonic transducer 320 relative to generator 310.

Figure 3:
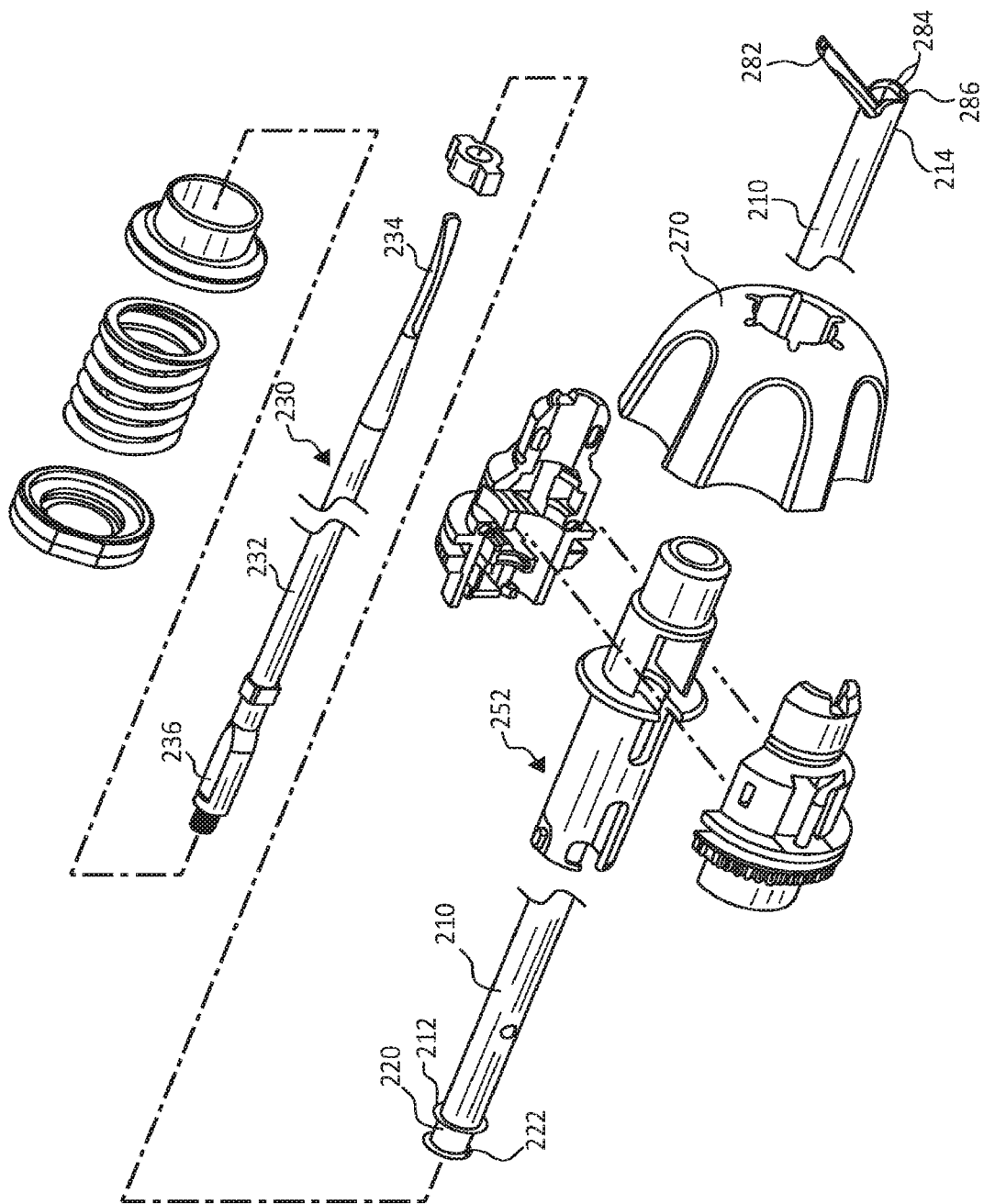
FIG. 3 is a perspective view of the elongated assembly of the ultrasonic surgical instrument of FIG. 1A with parts separated.

With reference to FIGS. 2 and 3, elongated assembly 200 includes an outer drive sleeve 210, an inner support sleeve 220 disposed within outer drive sleeve 210 and about which outer drive sleeve 210 is configured to slide, a waveguide 230 extending through inner support sleeve 220, a drive assembly 250 disposed about outer drive sleeve 210 and operably coupled between outer drive sleeve 210 and clamp trigger 130, and an end effector 280 disposed at the distal end of inner support sleeve 220. Elongated assembly 200 is configured to engage handle assembly 100 such that mechanical motion output of ultrasonic transducer 320 is transmitted along waveguide 230 to end effector 280 for treating tissue therewith, such that clamp trigger 130 is selectively actuatable to manipulate end effector 280, and such that rotation knob 270 is selectively rotatable to rotate elongated assembly 200 relative to handle assembly 100.

Outer drive sleeve 210 is slidably disposed about inner support sleeve 220. Outer drive sleeve 210 is fixed relative to drive tube 252 of drive assembly 250. Outer drive sleeve 210 and inner support sleeve 220 each include a proximal collar 212, 222, respectively, defined at the proximal end portion thereof, and each is operably coupled to jaw member 282 of end effector 280 at the distal end portion thereof.

Waveguide 230 extends through inner support sleeve 220. Waveguide 230 defines a body 232, a blade 234 extending from the distal end of body 232, and a proximal connector 236 extending from the proximal end of body 232. Blade 234 extends distally from inner support sleeve 220 and forms part of end effector 280 in that blade 234 is positioned to oppose jaw member 282 such that pivoting of j aw member 282 from the open position to the clamping position enables clamping of tissue between jaw member 282 and blade 234. Proximal connector 236 of waveguide 230 is configured to enable engagement of waveguide 230 with ultrasonic transducer 320 such that mechanical motion produced by ultrasonic transducer 320 is capable of being transmitted along waveguide 230 to blade 234 for treating tissue clamping between blade 234 and jaw member 282 or positioned adjacent to blade 234.

End effector 280 may be rotated relative to handle assembly 100 by rotating rotation knob 270. Once positioned as desired, clamp trigger 130 may be actuated to pivot jaw member 282 from the open position towards the clamping position to clamp tissue to be treated between jaw member 282 and blade 234. With tissue sufficiently clamped between jaw member 282 and blade 234, activation button 120 may be activated in either the "LOW" power mode or the "HIGH" power mode to initiate the supply power from battery assembly 400 to TAG 300 for driving ultrasonic transducer 320 to, in turn, transmit ultrasonic mechanical motion along waveguide 230 to blade 234 for treating tissue therewith, in either the "LOW" power mode or the "HIGH" power mode.

Figure 4:
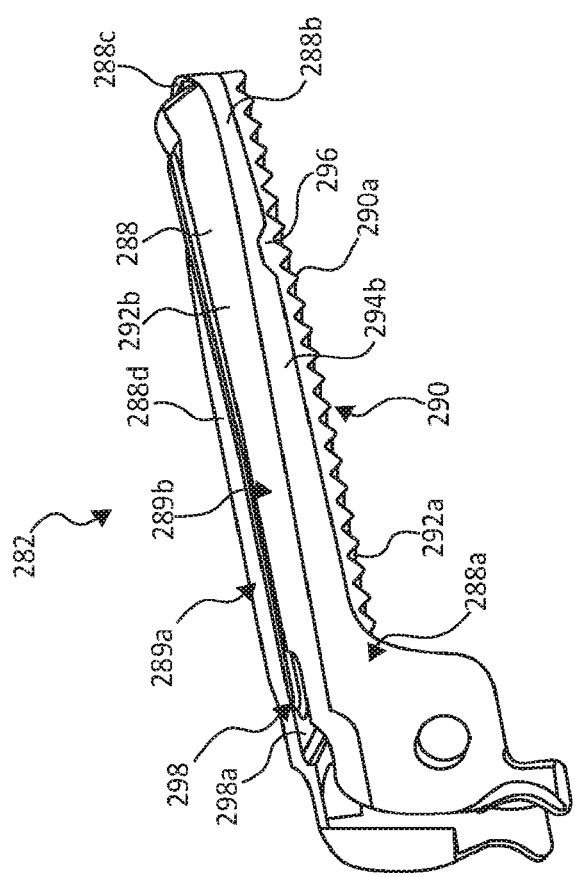
FIG. 4 is a perspective view of a jaw member of the end effector of the ultrasonic surgical instrument of FIG. 1A.

With additional reference to FIG. 4, jaw member 282 generally includes a support base 288, a jaw liner 290, and an elongated plate 298. Support base 288 of jaw member 282 has a relatively rigid construction to provide integrity to jaw member 282 such that jaw member 282 can apply pressure to tissue when end effector 280 is in the clamped configuration (FIG. 1B). Support base 288 has a proximal portion 288a and a distal portion 288b. Proximal portion 288a of support base 288 has a pair of spaced-apart jaw flanges 284 that are pivotably mounted at the distal end of inner support sleeve 220 to pivotably couple jaw member 282 to inner support sleeve 220, and a jaw foot 286 extending through an aperture 214 defined within outer drive sleeve 210 at the distal end thereof such that proximal translation outer drive sleeve 210 about inner support sleeve 220 and relative to end effector 280 pivots jaw member 282 from an open position to a clamping position.

Support base 288 of jaw member 282 defines a cavity 288d therein that extends longitudinally along proximal and distal portions 288a, 288b thereof. Cavity 288d extends through lower surface 292a of support base 288, a thickness of support base 288, and upper surface 292b of support base 288, and is surrounded by an inwardly-facing surface 289a of support base 288. Support base 288 further includes an outwardly-facing surface 289b. Cavity 288d is configured for receipt of jaw liner 290 and elongated plate 298. Jaw liner 290 is inserted into support base 288 from upper surface 292b of support base 288 (further from blade 234 of ultrasonic surgical instrument 10 as compared to lower surface 292a of support base 288).

Jaw liner 290 of jaw member 282 is fabricated from a compliant material that allows blade 234 of ultrasonic surgical instrument 10 to vibrate while in contact therewith without causing damage to blade 234 or other components of ultrasonic surgical instrument 10, and without compromising the hold on tissue grasped therebetween. Jaw liner 290 is configured to be situated in support base 288 such that blade 234 makes contact with jaw liner 290 rather than support base 288 when end effector 280 is in the clamped condition (FIG. 1B). Tissue-contacting surface 290a of jaw liner 290 has a plurality of teeth disposed along a length of jaw liner 290. Tissue-contacting surface 290a of jaw liner 290 protrudes from lower surface 292a of support base 288 the jaw liner 290.

Support base 288 includes first side wall (not shown) and second side walls 294b that cooperate to define the inwardly-facing surface 289a of support base 288 that surrounds cavity 288d on either side thereof. First side wall (not shown) and second side walls 294b are formed with one another at a rounded distal end portion 288c of support base 288. First side wall (not shown) and second side walls 294b of the support base 288 each include a notch 296 defined within the lower surface 292a thereof. Notches 296 are disposed towards the distal portions of the first (not shown) and second side walls 294b, although other locations are also contemplated. Since tissue-contacting surface 290a of jaw liner 290 protrudes from lower surface 292a of support base 288, notches 296 do not affect operation of jaw member 282, e.g., pivoting of jaw member 282 from the open position to the clamping position.

Figure 5:
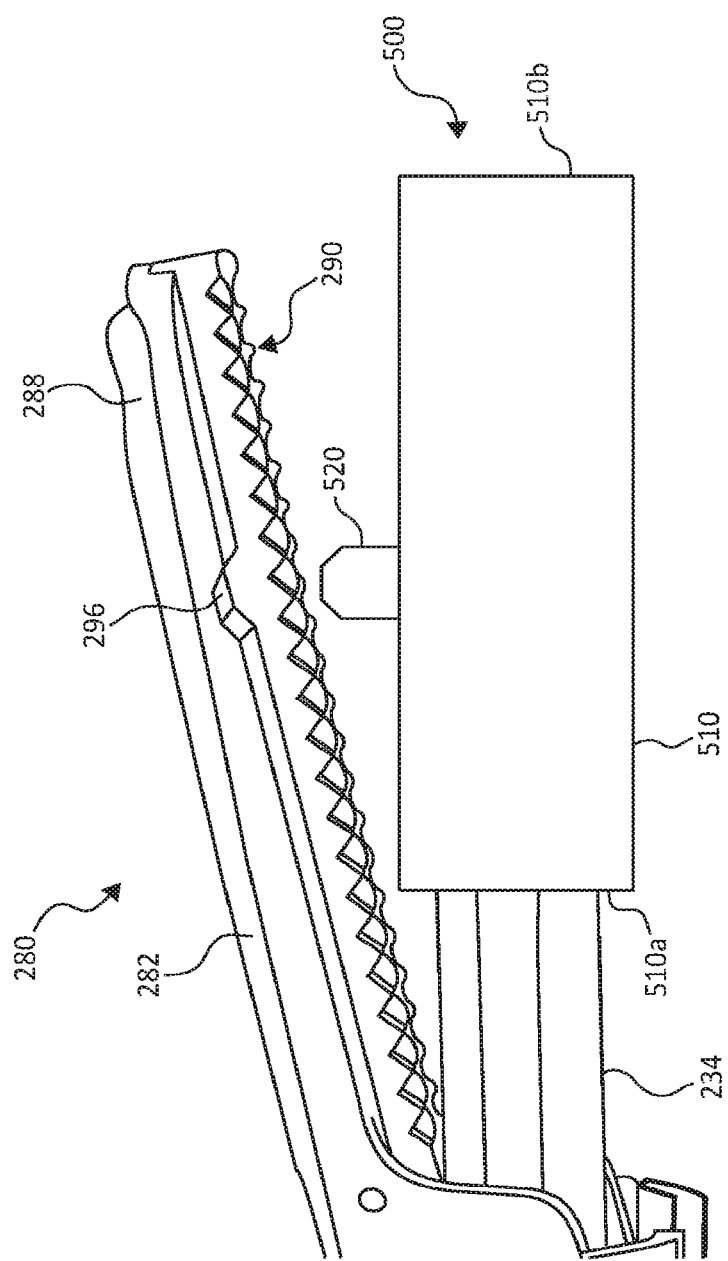
FIG. 5 is a perspective view of the end effector of the ultrasonic surgical instrument of FIG. 1A, including a sensor and a fixture coupled thereto for testing jaw force.

During manufacturing, the end effector 280 of the ultrasonic surgical instrument 10 is manufactured with a predetermined jaw force, however in repeating the manufacturing process there may be an inevitable variation in the actual manufactured jaw force of end effector 280. With reference to FIG. 5, in order to facilitate testing of the jaw force of end effector 280 of ultrasonic surgical instrument 10, between jaw member 282 and blade 234, the ultrasonic surgical instrument 10 may further include a testing assembly 500. Testing assembly 500 generally includes a fixture 510 and a sensor 520 configured to be coupled to fixture 510. Fixture 510 has a longitudinal opening extending from a proximal end portion 510a to a distal end portion 510b. Proximal end portion 510a of fixture 510 is configured for insertion of blade 234, and configured to secure blade 234 of end effector 280. Alternatively, blade 234 may be inserted from an open top side of fixture 510.

End effector 280 is positioned relative to fixture 510 such that sensor 520 is disposed adjacent notch 296. As a result of this configuration, sensor 520 is received within notch 296 upon clamping of end effector 280, to provide measurement of jaw force of end effector 280 between jaw member 282 and blade 234. In some embodiments, testing assembly 500 may include at least two sensor 520, one disposed adjacent each notch 296 towards the distal portions of the first (not shown) and second side walls 294b. Sensor 520, for example, may be, a force sensor, e.g., a load cell, or any other suitable sensor component capable of measuring and providing feedback with respect to a jaw force of end effector 280. Sensor 520 may additionally or alternatively determine a distance from notch 296 to a jaw pivot point of the end effector 280.

In operation, blade 234 of end effector 280 is inserted into fixture 510 of testing assembly 500, to secure blade 234. After positioning of blade 234 within fixture 510, clamp trigger 130 is actuated to pivot jaw member 282 from the open position towards the clamping position to clamp jaw liner 290 against blade 234. In this clamping position, sensor 520 engages notch 296 to measure the clamping force of end effector 280, which is the manufactured jaw force of the end effector 280. Upon measuring the manufactured jaw force of end effector 280, the measured manufactured jaw force is compared with a predetermined jaw force range to determine if the end effector 280 is within acceptable limits, e.g., within the predetermined jaw force range. In embodiments, the measured manufactured jaw force is stored in a memory associated with surgical instrument 10, e.g., of generator 310 of TAG 300, for use in determining an appropriate drive signal for driving the transducer 320 and/or for later retrieval.

In some embodiments, in the clamping position, sensor 520 (or another sensor) determines a distance from notch 296 to a jaw pivot point of the end effector 280. This distance may be used itself and/or in combination with the measured manufactured jaw force to determine whether surgical instrument 10 was manufactured within acceptable limits.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. A method of testing a jaw force of an ultrasonic surgical instrument, the method comprising:
    securing a blade of an end effector of the ultrasonic surgical instrument;
    clamping a jaw member of the end effector against the blade such that a sensor is received within a notch of the jaw member of the end effector; and
    measuring the jaw force of the end effector using the sensor.

2. The method according to claim 1, further comprising determining a distance of the sensor from a jaw pivot point of the end effector.

3. The method according to claim 1, wherein securing the blade includes inserting the blade into a fixture configured to hold the blade in place.

4. The method according to claim 1, wherein the sensor is a force sensor.

5. The method according to claim 1, wherein the sensor is a load cell.

6. The method according to claim 1, wherein the measured jaw force is the manufactured clamping force of the end effector.

7. The method according to claim 6, further comprising determining if the manufactured clamping force of the end effector is within a predetermined range.

8. The method according to claim 1, wherein the jaw member includes a support base and a jaw liner, wherein the notch is defined within the support base, and wherein the jaw liner is configured to clamp against the blade.

9. An ultrasonic system, comprising:
   an ultrasonic surgical instrument having an end effector configured to treat tissue between a jaw member and a blade of the end effector;
   a sensor configured for insertion into a notch of the jaw member for measurement of the jaw force of the end effector between the jaw member and the blade; and
   a fixture configured to secure the blade of the end effector.

10. The ultrasonic system according to claim 9, wherein the sensor is further configured to determine a distance from the sensor to a jaw pivot point of the end effector.

11. The ultrasonic system according to claim 9, wherein the sensor is a force sensor.

12. The ultrasonic system according to claim 9, wherein the sensor is a load cell.

13. The ultrasonic system according to claim 9, wherein the measured jaw force is the manufactured clamping force of the end effector.

14. The ultrasonic system according to claim 1, wherein the jaw member includes a support base and a jaw liner, wherein the notch is defined within the support base, and wherein the jaw liner is configured to clamp against the blade.

\* \* \* \* \*